United States Patent [19]

Lin et al.

[11] Patent Number: 5,756,814
[45] Date of Patent: May 26, 1998

[54] VINYL COMPOUND, ITS SYNTHETIC INTERMEDIATES AND PROCESSES FOR PRODUCING THE SAME

[75] Inventors: Leng-Tain Lin, Kitaibaraki; Kenji Iimura; Takehiro Sonoi, both of Kitaibaraki

[73] Assignee: Nippon Mektron, Limited, Tokyo, Japan

[21] Appl. No.: 880,811

[22] Filed: Jun. 23, 1997

[30] Foreign Application Priority Data

Jun. 28, 1996 [JP] Japan ................... 8-188438

[51] Int. Cl.⁶ ............................... C07C 69/88
[52] U.S. Cl. ..................... 560/65; 562/474; 562/409; 568/319; 568/308; 568/663
[58] Field of Search ................... 560/65; 562/474, 562/409; 568/319, 308, 663

[56] References Cited

PUBLICATIONS

CAS Online Printout, Abstract 108:186808, RN 114142-56-2, 1987.

CAS Online Printout, Abstract 105:171929, RN 104729-63-7, 1985.

*Primary Examiner*—Samuel Barts
*Attorney, Agent, or Firm*—Kenyon & Kenyon

[57] ABSTRACT

(1) $CF_2=CFO(CF_2)_nCOOR$ is allowed to react with chlorine or bromine to obtain $CF_2XCFXO(CF_2)_nCOOR$, (2) which is allowed to react with a Grignard reagent $MgBrC_6H_3(CH_3)_2$ to convert the terminal group to $-COC_6H_3(CH_3)_2$, (3) followed by reaction with diethylaminosulfur trifluoride to convert $-COC_6H_3(CH_3)_2$ to $-CF_2C_6H_3(CH_3)_2$, (4) followed further by oxidation of the resulting methyl group and by esterification to convert the methyl group to $-CF_2C_6H_3(COOR)_2$ and (5) followed by dechlorination or debromination to obtain $CF_2=CFO(CF_2)_nCF_2C_6H_3(COOR)_2$. The resulting bifunctional vinyl ether compound having an aromatic ring is a novel compound and can be used as a copolymer component for fluorine-containing elastomers.

8 Claims, No Drawings

VINYL COMPOUND, ITS SYNTHETIC INTERMEDIATES AND PROCESSES FOR PRODUCING THE SAME

BACKGROUND OF THE INVENTION

1. Field of the Invention

The present invention relates to a novel vinyl ether compound, its synthetic intermediates and a processes for producing the same, and more particularly to a novel vinyl ether compound effective as a copolymer component of fluorine-containing elastomer, its synthetic intermediates and a processes for producing the same.

2. Related Art

Fluorine-containing elastomers are distinguished not only in the heat resistance, but also in the oil resistance and chemical resistance. Recently, bifunctional vinyl ethers copolymerizable as cross-linking site monomers into fluorine-containing elastomers having such distinguished charactristics have been highlighted.

SUMMARY OF THE INVENTION

An object of the present invention is to provide a novel bifunctional vinyl ether compound having an aromatic ring, which can serve as an effective vinyl ether compound as a copolymer component of fluorine-containing elastomer.

A novel vinyl ether compound according to the present invention can be represented by the following general formula:

$$CF_2=CFO(CF_2)_nCF_2C_6H_3(COOR)_2$$

where R is a hydrogen atom or a lower alkyl group and n is an integer of 1 to 5.

DETAILED DESCRIPTION OF THE INVENTION

The vinyl ether compound according to the present invention can be produced by a series of the following steps:

$$CF_2=CFO(CF_2)_nCOOR' \rightarrow CF_2XCFXO(CF_2)_nCOOR' \quad (1)$$

The halogen addition reaction can be readily carried out by bubbling a chlorine gas into a lower alkyl ester compound or dropwise adding bromine thereto, preferably under ultraviolet irradiation. The lower alkyl ester compound used as a starting material can be prepared by subjecting $FOC(CF_2)_n COOR'$, where m: n−1, to addition reaction with hexafluoropropeneoxide and subjecting the resulting $FOCCF(CF_3)O(CF_2)_mCOOR'$ to heat decomposition in the presence of an alkali metal carbonate. The initial starting material $FOC(CF_2)_mCOOR'$ can be obtained by reaction of $FOC(CF_2)_m COF$ with R'OH.

$$CF_2XCFXO(CF_2)_nCOOR'+MgBrC_6H_3(CH_3)_2) \rightarrow CF_2XCFXO(CF_2)_nCOC_6H_3(CH_3)_2 \quad (2)$$

The Grignard reagent $MgBrC_6H_3(CH_2)_2$ can be obtained generally by reaction of bromobenzene having 3,4-dimethyl groups with metallic magnesium. Reaction of the ester compound with the Grignard reagent can be carried out by dropwise addition of the Grignard reagent to a solution of the ester compound, using an ether compound such as tetrahydrofuran, diethyl ether, etc. as a solvent, while keeping the temperature at about −60° to about −50° C., followed by stirring at a temperature of about −60° to 0° C. for about 1 to about 2 hours.

$$CF_2XCFXO(CF_2)_nCOC_6H_3(CH_3)_2 \rightarrow CF_2XCFXO(CF_2)_nCF_2C_6H_3(CH_3)_2 \quad (3)$$

The reaction can be readily carried out by dropwise addition of diethylaminosulfur trifluoride $(C_2H_5)_2NSF_3$ under a cooling condition with iced water, followed by stirring at a temperature of about 10° to about 20° C.

$$CF_2XCFXO(CF_2)_nCF_2C_6H_3(CH_3)_2 \rightarrow CF_2XCFXO(CF_2)_nCF_2C_6H_3(COOR)_2 \quad (4)$$

The reaction is carried out firstly by conversion of methyl groups to carboxyl groups through stepwise addition of oxygen at a temperature of about 100° to about 200° C. in an autoclave, using a solvent such as acetic acid, etc. and a catalyst such as cobalt acetate, manganese acetate, etc. in the presence of an aqueous hydrobromic acid solution capable of enhancing the catalytic activity, and then by esterification reaction. The esterification reaction can be carried out according to any desired procedure, for example, by reaction with a lower alkyl halide under basic conditions, using an aprotic polar solvent such as hexamethylphosphorylamide. The reaction products includes a R=H compound.

$$CF_2XCFXO(CF_2)_nCF_2C_6H_3(COOR)_2 \rightarrow CF_2=CFO(CF_2)_nCF_2C_6H_3(COOR)_2 \quad (5)$$

Dechlorination reaction or debromination reaction for the vinyl etherification can be carried out by charging powdery zinc, a solvent such as demethyl formamide, dimethyl acetamide, methanol, ethanol, etc. and iodine as a zinc activating agent into a reactor, heating the reactor to a temperature of about 20° to about 150° C., and then dropwise addition of a solution of the ether compound dissolved in the solvent thereto.

The novel vinyl ether compound obtained by a series of these steps is copolymerized with tetrafluoroethylene and perfluoro(lower alkyl vinyl ether) or perfluoro(lower alkoxy-lower alkyl vinyl ether) to form a fluorine-containing elastomer copolymer.

For the perfluoro(lower alkyl vinyl ether), perfluoro(methyl vinyl ether) can be usually used. For the perfluoro(lower alkoxy-lower alkyl vinyl ether), the following compounds an be used:

| | |
|---|---|
| $CF_2=CFOCF_2CF(CF_3)OC_nF_{2n+1}$ | (n:1 ~ 5) |
| $CF_2=CFO(CF_2)_3OC_nF_{2n+1}$ | (n:1 ~ 5) |
| $CF_2=CFOCF_2CF(CF_3)O(CF_2O)_mC_nF_{2n+1}$ | (n:1 ~ 5; m:1 ~ 3) |
| $CF_2=CFO(CF_2)_2OC_nF_{2n+1}$ | (n:1 ~ 5) |

Among these compounds, those whose $C_nF_{2n+1}$ group is a $CF_3$ group are preferably used.

Copolymerization can be carried out according to any desired procedure, for example, by emulsion polymerization, suspension polymerization, solution polymerization, bulk polymerization, etc., using about 30 to about 70% by mole of tetrafluoroethylene, about 65 to about 25% by mole of perfluoro (lower alkyl vinyl ether) or perfluoro(lower alkoxy-lower alkyl vinyl ether) and about 0.1 to 5% by mole of the present vinyl ether compound, sum total being 100% by mole.

Among them, emulsion polymerization is preferable from the view point of economy. Emulsion polymerization reaction can be carried out generally at a temperature of about 40° to about 85° C. under a pressure of about 3 to about 8 MPa, using a water-soluble inorganic peroxide or its redox system as a catalyst and ammonium perfluorooctanoate, etc. as a surfactant. The terpolymer can be further copolymerized with a fluoroolefin, an olefin, a vinyl compound, etc. to such an extent as not to inhibit the copolymerization reaction and deteriorate physical properties of vulcanization products, for example, not more than about 20% by mole, on the basis of the resulting fluorine-containing elastomer copolymer.

Vulcanization of the resulting fluorine-containing elastomer copolymer can be carried out by adding about 0.5 to about 5 parts by weight, preferably about 1 to about 2 parts by weight to 100 parts by weight of the terpolymer, of an aliphatic diamine such as hexamethylenediamine, ethylene diamine, etc., or an aromatic diamine represented by the following general formula:

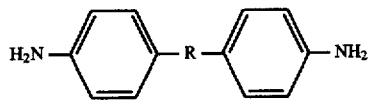

where R is $CF_2$, $C(CF_3)_2$, O, $SO_2$, etc., followed by press vulcanization at a temperature of about 160° to about 250° C. If required, oven vulcanization (secondary vulcanization) can be carried out. Carbon black, silica, etc. can be added as a filler to the mixture for vulcanization, if required.

The present invention provides a vinyl ether compound represented by the following general formula:

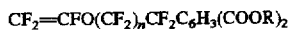

where R is a hydrogen atom or a lower alkyl group and n is an integer of 1 to 5, which can act as a cross-linking site for the vulcanization, when copolymerized into a fluorine-containing elastomer.

PREFERRED EMBODIMENTS OF THE INVENTION

The present invention will be described in detail below, referring to Example and Reference Example.

EXAMPLE (1) 964.5 g (2.558 moles) of $CF_2\!=\!CFO(CF_2)_3COOCH_3$ was charged into a reactor having a capacity of 2 liters and subjected to reaction by bubbling 248 g (3.493 moles) of chlorine therein over 5 hours, while keeping the reactor inside temperature so as not to exceed 80° C. After the reaction, the reaction mixture was washed once with an aqueous sodium hydrogen carbonate solution and then twice with water, followed by drying over magnesium sulfate and distillation under reduced pressure, whereby 819.5 g of $CF_2ClCFClO(CF_2)_3COOCH_3$ was obtained as a fraction of boiling point of 105° C./80 mmHg (yield: 71.5%)

(2) 54 g (2.261 mole) of Mg was charged into a reactor having a capacity of 2 liters. Then, the reactor was flushed with a nitrogen gas, and a solution containing 597 g (2.260 mole) of 1-bromo-3,4-dimethylbenzene dissolved in 500 ml of tetrahydrofuran was dropwise added to the reactor over about 3 hours, while keeping the reactor inside temperature so as not to exceed 60° C. After the dropwise addition, the mixture was stirred for one hour, while checking whether the metallic Mg substantially disappeared to prepare a Grignard reagent.

Then, 774 g (2.055 moles) of the chlorine adduct obtained in the foregoing step (1) and 1 liter of tetrahydrofuran were charged into a reactor having a capacity of 5 liters and the reactor was cooled down to −60° C. with dry ice/methanol. Then, the Grignard reagent was dropwise added thereto over about 2 hours and the mixture was stirred for one hour, while keeping the same temperature as above. Then, the mixture was subjected to temperature elevation to 0° C. at a temperature elevation rate of 10° C./30 min, and then stirred for one hour. The reaction was completed by addition of 1.2 liters of 2N hydrochloric acid thereto.

The resulting reaction mixture was decanted, and the organic layer was washed with an aqueous sodium chloride saturated solution. The washing solution and the aqueous layer were joined together and subjected to extraction with the same volume of ethyl acetate. The extract was washed with an aqueous sodium chloride saturated solution, and the washed extract and the organic layer was joined together, and dried over magnesium sulfate. After removal of the solvent by distillation, 503.8 g of the following compound [IV] was obtained as a fraction of boiling point 135° C./3 mmHg (yield : 54.4%):

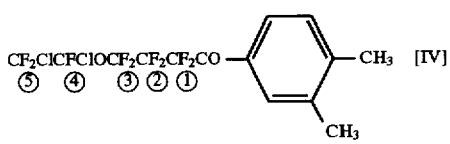

$^{19}$F-NMR ($CF_3COOH$ base):

① 34.3 ppm (2F)
② 46.3 ppm (2F)
③ 5.3 ppm (2F)
④ −1.0 ppm (1F)
⑤ −11.7 ppm (2F)

$^{1}$H-NMR (TMS base):

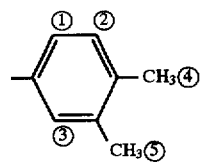

① 7.80 ppm (1H, d, J=9.0Hz)
② 7.27 ppm (1H, d, J=9.0Hz)
③ 7.84 ppm (1H, s)
④ 2.31 ppm (3H, s)
⑤ 2.32 ppm (3H, s)

Infrared absorption spectrum:

2975 cm$^{-1}$ (−$CH_3$)
1705 cm$^{-1}$ (C=O)
1605 cm$^{-1}$ (aromatic ring)
1570 cm$^{-1}$ (aromatic ring)

(3) 319 g (0.708 moles) of reaction product [IV] from the foregoing step (2) was charged into a reactor having a capacity of 1 liter and cooled with iced water, and then 128 ml (0.970 mole) of diethylaminosulfur trifluoride was dropwise added thereto over about 30 minutes. After the dropwise addition, the mixture was stirred at room temperature overnight, and then the reaction mixture was slowly poured into an aqueous sodium hydrogen carbonate solution. The resulting organic layer was washed with water, dried over magnesium sulfate and distilled under reduced pressure, whereby 185.4 g of the following compound [III] was obtained as a fraction of boiling point 110° C./3 mmHg [yield: 55.4%]:

$^{19}$F-NMR ($CF_3COOH$ base):

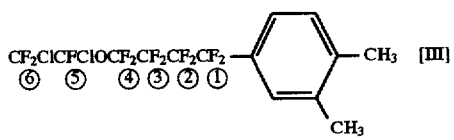

| | | |
|---|---|---|
| ① | 31.5 ppm | (2F) |
| ② | 42.5 ppm | (2F) |
| ③ | 45.5 ppm | (2F) |
| ④ | 4.8 ppm | (2F) |
| ⑤ | −1.5 ppm | (1F) |
| ⑥ | −7.0 ppm | (2F) |

$^1$H-NMR (TMS base):

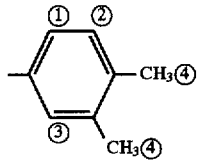

| | | |
|---|---|---|
| ① | 7.30 ppm | (1H, d, J=7.7Hz) |
| ② | 7.22 ppm | (1H, d, J=7.7Hz) |
| ③ | 7.33 ppm | (1H, s) |
| ④ | 2.31 ppm | (6H, s) |

(4) 2.8 g of cobalt acetate, 2.7 g of manganese acetate and 112.6 g (0.238 moles) of reaction product [III] from the foregoing step (3) were charged into an autoclave having a capacity of 500 ml, and the autoclave was subjected to pressure reduction. Then, 2.2 ml (14.6 millimoles) of an aqueous 47% hydrobromic acid solution and 150 ml of acetic acid were charged thereto by spontaneous suction. The reaction temperature was elevated to 110° C., and stepwise addition of oxygen was repeated until no more pressure decrease occurred even if the gauge pressure was ultimately elevated to 13 kg/cm$^2$. After release of the autoclave inside pressure at room temperature by purging, the reaction mixture was subjected to temperature elevation to 110° C., and stepwise addition of oxygen was repeated also throughout next day until no more pressure decrease occurred. After the reaction, the reaction mixture was washed three times with 150 ml of water and insoluble matters were dissolved in 300 ml of ethyl acetate. Then, the ethyl acetate solution was washed with the same volume of an aqueous sodium chloride saturated solution, dried over magnesium sulfate and subjected to removal of the solvent by distillation.

202 g of the thus obtained crude product, 400 ml of hexamethylphosphoramide and 182 ml of an aqueous sodium hydroxide solution were charged into a reactor having a capacity of 2 liters, and 137 ml of methyl iodide was dropwise added thereto over about 30 minutes, while cooling the reactor with iced water. After the dropwise addition, the mixture was stirred at room temperature overnight, and then 600 ml of 2N hydrochloric acid was added thereto, followed by extraction with ethyl acetate. The extract was washed with water, dried over magnesium sulfate, and subjected to removal of the solvent by distillation and to purify the residue by column chromatography [developing solvent: solvent mixture of ethyl acetate/n-hexane (1:5 by volume)], whereby 41.9 g of the following reaction product [II] was obtained (yield: 31.4%):

$^{19}$F-NMR (CF$_3$COOH base):

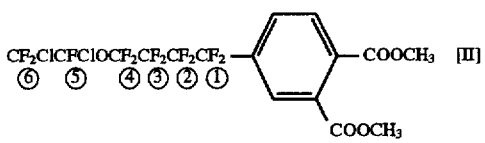

| | | |
|---|---|---|
| ① | 32.0 ppm | (2F) |
| ② | 42.5 ppm | (2F) |
| ③ | 45.0 ppm | (2F) |
| ④ | 5.3 ppm | (2F) |
| ⑤ | −1.6 ppm | (1F) |
| ⑥ | −12.1 ppm | (2F) |

$^1$H-NMR (TMS base):

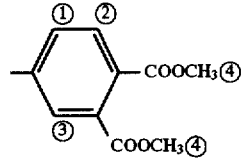

| | | |
|---|---|---|
| ① | 7.80 ppm | (1H, d J=8.25Hz) |
| ② | 7.83 ppm | (1H, d J=8.25Hz) |
| ③ | 8.01 ppm | (1H, s) |
| ④ | 3.95 ppm | (6H, s) |

Infrared absorption spectrum:

2952 cm$^{-1}$ (—CH$_3$)
1738 cm$^{-1}$ (C=O)
1618 cm$^{-1}$ (aromatic ring)
1578 cm$^{-1}$ (aromatic ring)

(5) 9.3 g (110 millimole) of zinc powder and 50 ml of dimethyl formamide were charged into a reactor having a capacity of 200 ml and the mixture was subjected to temperature elevation to 110° C. Then, a solution containing 62 g (110 millimole) of reaction product [II] from the foregoing step (4) dissolved in 10 ml of dimethyl formamide was dropwise added thereto over about 30 minutes. After the dropwise addition, a solution containing 1.4 g of iodine dissolved in 5 ml of dimethyl formamide was poured therein, and the mixture was stirred at 11° C. for 2 hours. After the reaction, the reaction mixture was decanted, and the residual zinc was washed with 20 ml of dimethyl formamide. The washing dimethyl formamide solution and the decanted dimethyl formamide solution were joined together, followed by neutralization with 2N hydrochloric acid and extraction with n-hexane. The extract was washed with water, dried over magnesium sulfate and subjected to removal of the solvent by distillation and to purify the residue by column chromatography [developing solvent: the same as used in the foregoing step (4)], whereby 42.3 g of the following reaction product [I] was obtained (yield: 78.0%):

$^{19}$F-NMR (CF$_3$COOH base):

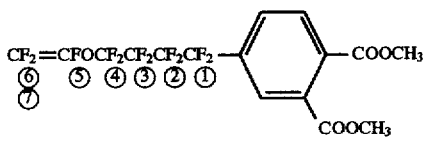

| | | |
|---|---|---|
| ① | 30.8 ppm | (2F) |
| ② | 41.7 ppm | (2F) |
| ③ | 43.3 ppm | (2F) |
| ④ | 6.6 ppm | (2F) |
| ⑤ | 33.0 ppm | (1F) |
| ⑥ | 40.3 ppm | (1F) |
| ⑦ | 53.2 ppm | (1F) |

REFERENCE EXAMPLE (1) 60.3 ml of distilled water, 1.55g of ammonium perfluorooctanoate and 2.72 g of Na$_2$HPO$_4$·12H$_2$O were chrged into a stainless steel autoclave having a capacity of 500 ml, and the autoclave was flushed with a nitrogen gas and then subjected to pressure reduction. Then, 22.5 g (0.225 moles) of tetrafluoroethylene and 37.4 g (0.225 moles) of perfluoro (methyl vinyl ether) were successively charged therein, and the mixture was subjected to temperature elevation to 50° C. 4.51 g (9.2 millimoles) of ultimate reaction product [I] obtained in the foregoing Example was charged therein by a pressure feed pump, then 0.47 g of sodium sulfite and 2.33 g of ammonium persulfate were charged therein as 43 ml of aqueous solutions, respectively, to initiate polymerization reaction. After continuation of polymerization reaction for 6 hours, the autoclave was cooled and the residual gas was purged therefrom to obain an aqueous latex.

The thus obtained aqueous latex was added to 2 liters of an aqueous sodium chloride saturated solution at 70° C. to coagulate the formed polymers. The coagulates were recovered by filtration, washed with water and dried at 70° C. under the normal pressure for 12 hours and 120° C. under reduced pressure for 12 hours, whereby 38.2 g of white, rubbery terpolymer was obtained. By infrared absorption spectrum it was found that the terpolymer had absorptions at 1578 cm$^{-1}$ and 1618 cm$^{-1}$ and that the compound [I] was copolymorized in the terpolymer.

| Polymer composition by $^{19}$F-NMR: | |
|---|---|
| Tetrafluoroethylene | 53.1% by mole |
| Perfluoro(methyl vinyl ether) | 45.1% by mole |
| Compound [I] | 1.8% by mole |

Reduced viscosity η sp/c: 0.6 dl/g, as measured at 35° C. for 0.1 wt % solution in perfluoro(2-butyltetrahydrofuran)

(2) 5 parts by weight of MT carbon black and 1.4 parts by weight of 4,4'-diaminodiphenyl ether were added to 100 parts by weight of the resulting terpolymer, and the mixture was kneaded through two rolls rubber mill. Increase in vulcanization torque was found by measuring torque at 200° C. for 60 minutes by Curastometer V (made by Oriontex K.K., Japan), showing that the vulcanization reaction was under way.

What is claimed is:

1. A vinyl ether compound represented by the following general formula:

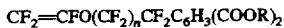

where R is a hydrogen atom or a lower alkyl group and n is an integer of 1 to 5.

2. An ether compound represented by the following general formula:

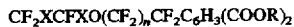

where R is a hydrogen atom or a lower alkyl group; X is a chlorine atom or a bromine atom; and n is an integer of 1 to 5.

3. An ether compound represented by the following general formula:

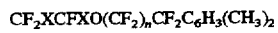

where X is a chlorine atom or a bromine atom and n is an integer of 1 to 5.

4. An ether compound represented by the following general formula:

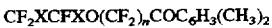

where X is a chlorine atom or a bromine atom and n is an integer of 1 to 5.

5. A process for producing a vinyl ether compound represented by the following general formula:

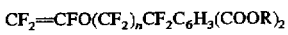

where R is a hydrogen atom or a lower alkyl group and n is an integer of 1 to 5, which comprises dechlorinating or debromininating an ether compound represented by the following general formula:

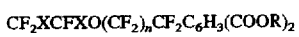

where R and n have the same meanings as defined above and X is a chlorine atom or a bromine atom.

6. A process for producing an ether compound represented by the following general fomula:

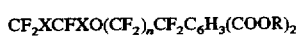

where R is a hydrogen atom or a lower alkyl group; X is a chlorine atom or a bromine atom; and n is an integer of 1 to 5, which comprises oxidizing an ether compound represented by the following general formula:

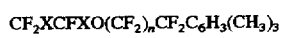

where X and n have the same meanings as defined above, followed by esterification.

7. A process for producing an ether compound represented by the following general formula:

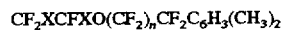

where X is a chlorine atom or a bromine atom and n is an integer of 1 to 5, which comprises allowing an ether compound represented by the following general formula:

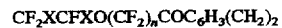

where X and n have the same meanings as defined above, to react with diethylaminosulfur trifluoride.

8. A process for producing an ether compound represented by the following general formula:

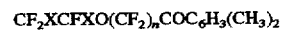

where X is a chlorine atom or a bromine atom and n is an integer of 1 to 5, which comprises allowing an ester compound represented by the following general formula:

where R' is a lower alkyl group; X is a chlorine atom or a bromine atom; and n is an integer of 1 to 5, to react with a Grignard reagent represented by the following formula:

* * * * *